United States Patent
Gao (10) Patent No.: US 11,197,941 B1
(45) Date of Patent: Dec. 14, 2021

(54) AROMA DIFFUSER

(71) Applicant: SHENZHEN SUNTEK ELECTRONIC CO., LTD., Shenzhen (CN)

(72) Inventor: Yong Gao, Shenzhen (CN)

(73) Assignee: SHENZHEN SUNTEK ELECTRONIC CO., LTD., Shenzhen (CN)

( * ) Notice: Subject to any disclaimer, the term of this patent is extended or adjusted under 35 U.S.C. 154(b) by 0 days.

(21) Appl. No.: 17/467,445

(22) Filed: Sep. 6, 2021

(30) Foreign Application Priority Data

Feb. 8, 2021 (CN) .......................... 202120354216.3
Aug. 27, 2021 (CN) .......................... 202122054276.6

(51) Int. Cl.
*A61L 9/14* (2006.01)

(52) U.S. Cl.
CPC ........... *A61L 9/14* (2013.01); *A61L 2209/134* (2013.01)

(58) Field of Classification Search
CPC . A61L 9/14; A61L 2209/133; A61L 2209/134
See application file for complete search history.

(56) References Cited

U.S. PATENT DOCUMENTS

| 8,939,386 | B2 * | 1/2015 | Robert | ...................... B05B 7/30 |
| | | | | 239/346 |
| 9,511,166 | B1 * | 12/2016 | Li | .......................... A61M 11/06 |
| 10,092,918 | B1 * | 10/2018 | Levy | ........................ A61L 9/14 |

* cited by examiner

*Primary Examiner* — Timothy C Cleveland
(74) *Attorney, Agent, or Firm* — Cheng-Ju Chiang (57) ABSTRACT

An aroma diffuser comprises a host and an aromatherapy nebulizer; the host has an air pump received therein; the air pump has an air inlet port and an air outlet port; the aromatherapy nebulizer comprises a nebulizer cap and an essential oil bottle with a dip tube extending from the nebulizer cap into the essential oil bottle for sucking liquid essential oil up. The host sets a mounting ring extending outwards from a sidewall thereof, the aromatherapy nebulizer is installed in the mounting ring in such way that the aromatherapy nebulizer is able to be plugged in or pulled out up and down through the mounting ring, thereby the aromatherapy nebulizer is installed externally to the host.

20 Claims, 7 Drawing Sheets

AROMA DIFFUSER

FIELD OF THE INVENTION

The present invention relates to an aroma device, and more particularly, to an aroma diffuser.

BACKGROUND OF THE INVENTION

The aroma diffuser generally comprises a pressure can, an atomizer and an essential oil bottle filled with essential oil therein. The aroma diffuser can atomize the essential oil and then spray a fine mist of liquefied aromatic substance through a spray nozzle. The existing diffuser has separate air duct. Specifically, the air duct is a part with a small hole, which is difficult to assembly and is easy to damage. The separate air duct in the aroma atomizer is prone to displacement, and results in low atomization efficiency or even loss of function. Existing aroma diffusers generally has the essential oil bottle installed inside the main body, which is inconvenient to replace the essential oil bottle or observe the amount of essential oil.

SUMMARY OF THE INVENTION

A main object of the present invention is to provide an aroma diffuser to solve the problems that the existing aroma diffuser generally has the essential oil bottle installed inside, it is inconvenient to replace the essential oil bottle or observe the amount of essential oil.

Another object of the present invention is to provide an aroma diffuser to solve the problems that the existing aroma diffuser has a nebulizer cap with separable air duct, it is difficult to assemble, easy to be damaged or displacement.

To achieve these and other objects of the present invention, an aroma diffuser comprises an air pump and an aromatherapy nebulizer; the host has an air pump received therein; the air pump has an air inlet port and an air outlet port; the aromatherapy nebulizer comprises a nebulizer cap and an essential oil bottle with a dip tube extending from the nebulizer cap into the essential oil bottle for sucking liquid essential oil up. The host sets a mounting ring extending outwards from a sidewall thereof, the aromatherapy nebulizer is installed in the mounting ring in such way that the aromatherapy nebulizer is able to be plugged in or pulled out up and down through the mounting ring, thereby the aromatherapy nebulizer is installed externally to the host. The nebulizer cap comprises a bottom wall and a side wall around the bottom wall which has an upper sidewall defining an air chamber therein, and has a lower sidewall connected with the essential oil bottle; the aromatherapy nebulizer sets a spray nozzle communicating the air chamber with the external environment; the air chamber is communicated with the air outlet port of the air pump for transporting compressed air from the air pump into the air chamber, and is communicated with the dip tube for transporting the liquid essential oil from essential oil bottle into the air chamber for forming essential oil mist which is ejected to the external environment through the spray nozzle.

Preferably, the mounting ring substantially is an annular wall which is open and through up and down, and is adapted for the nebulizer cap; the upper sidewall around the bottom wall of the nebulizer cap forms an opening top and defines the air chamber therein; the aromatherapy nebulizer further comprises a top cover to close the opening top of the nebulizer cap; and the spray nozzle is formed in the top cover.

In some embodiment, the sidewall of the host for setting the mounting ring has a concave curved surface for holding the aromatherapy nebulizer; the concave curved surface of the sidewall has a shape adapted for the essential oil bottle and the nebulizer cap.

In some embodiment, the mounting ring is integrally formed in one piece with the sidewall of the host, and protrudes outwards on the sidewall; or, the mounting ring is fixed inside the host via a fastening piece formed on the mounting ring, and the mounting ring extends outwards from an opening defined in the sidewall of the host; or, the mounting ring is fixed on the sidewall of the host via fastening structures.

In some embodiment, an annular wall of the mounting ring defines a through hole for connecting airflow from the air outlet port of the air pump to the air chamber in the nebulizer cap when the aromatherapy nebulizer is installed in the mounting ring; the nebulizer cap defines an air inlet port communicated with the air chamber, the air inlet port of the nebulizer cap is aligned and connected with the through hole of the mounting ring when the aromatherapy nebulizer is installed in the mounting ring.

In some embodiment, an air connecting piece with an air passage inside is set in the host and extends in the through hole of the mounting ring; one end of the air connecting piece is connected with the air outlet port of the air pump, and the other end of the air connecting piece pass through the through hole of the mounting ring and extends to an inner wall of the mounting ring, whereby the air passage inside the air connecting piece connects the air outlet of the air pump with the air inlet port of the nebulizer cap when the aromatherapy nebulizer is installed in the mounting ring.

In some embodiment, when the aromatherapy nebulizer is installed in the mounting ring, the mounting ring is sleeved around the outside of the nebulizer cap, and the nebulizer cap is engaged with the mounting ring for fastening the aromatherapy nebulizer in the mounting ring.

In some embodiment, the nebulizer cap forms a protruding flange thereon, when the aromatherapy nebulizer is inserted into the mounting ring, the protruding flange is clamped on a top edge of the mounting ring; the protruding flange is a protruding ring around the sidewall of the nebulizer cap; the protruding ring has a larger diameter than that of the mounting ring; the nebulizer cap has a circular shape with an annular sidewall and a circular bottom wall.

In some embodiment, the nebulizer cap and the mounting ring form positioning structures therebetween; the positioning structures comprising one or more of a clamping structure, a fitting structuring, or protrusion/groove structures.

In some embodiment, the sidewall of the nebulizer cap forms one or more ribs along a height of the sidewall; the mounting ring is correspondingly provided with one or more receiving grooves or ribs on an inner wall thereof, thereby the nebulizer cap is fitted in the mounting ring with the one or more receiving grooves or ribs on the inner wall of the mounting ring engaged with the one or more ribs on the sidewall of the nebulizer cap, so that the rotation of the nebulizer cap relative to the mounting ring is limited, and the air inlet port of the nebulizer cap keeps aligned and connected with the through hole of the mounting ring when the aromatherapy nebulizer is installed in place.

In some embodiment, the nebulizer cap forms several ribs vertically and parallel spaced on the sidewall of the nebulizer cap; the mounting ring forms several ribs vertically and parallel spaced on the inner wall of the mounting ring along a height of the mounting ring so as to abut against the ribs on the sidewall of the nebulizer cap when the nebulizer cap is fitted in the mounting ring.

In some embodiment, the nebulizer cap and the mounting ring form grooves/protrusion engaging structure for positioning and limiting the nebulizer cap in the mounting ring.

Further, the nebulizer cap forms a groove on the sidewall thereof, and the mounting ring forms a protrusion upwards from a top edge thereof, and the protrusion is able to be received the groove; the groove is defined in the protruding flange.

In some embodiment, the nebulizer cap integrally forms an air duct and an essential oil output duct in one piece together; the air duct connects the air outlet port of the air pump with the air chamber in the nebulizer cap so as to deliver compressed air from the air pump to the air chamber; the essential oil output duct connects the dip tube with the air chamber so as to deliver the liquid essential oil sucked in the dip tube into the air chamber.

In some embodiment, the air duct is formed on the bottom wall of the nebulizer cap, an inlet end of the air duct passes through the sidewall of the nebulizer cap and forms an air inlet port of the nebulizer cap communicated with the air chamber via the air duct, and an outlet end of the air duct is located in the air chamber and forms an outlet port; the essential oil output duct passes through the bottom wall of the nebulizer cap, a lower end thereof connects the dip tube, and a top end thereof extends upwards into the air chamber and forms an outlet port.

Preferably, the outlet ports of the air duct and the essential oil output duct are adjacent to each other; and the outlet port of the air duct is located at top side the outlet port of the essential oil output duct, whereby the airflow from the outlet port of the air duct blows to the outlet port of the essential oil output duct.

In some embodiment, the outlet end of the air duct is tapered and narrowed towards the outlet port of the air duct; the top end of the essential oil output duct is tapered and narrowed towards the outlet port of the essential oil output duct; a diameter of the outlet port of the air duct ranges from 0.05 mm to 1 mm; a diameter of the outlet port of the essential oil output duct ranges from 0.1 mm to 2 mm; a horizontal distance between the outlet port of the air duct and the outlet port of the essential oil output duct is 0.2 mm-5 mm.

In some embodiment, the nebulizer cap is circular with a circular bottom wall and an annular sidewall, the outlet ports of the air duct and the essential oil output duct extend at a center of the circular bottom wall; the essential oil output duct is arranged along a vertical center axis of the circular bottom wall. The air duct and the essential oil output duct are integrated with the nebulizer cap in an injection molding of plastic materials.

In some embodiment, a pair of extending plates is set beside the outlet port of the air duct so as to forms an extended airflow passage of the air duct, both the outlet ports of the air duct and the essential oil output duct are located between the pair of extending plates; the pair of extending plates are parallel to each, one end of each plate is fitted on and connected with the outlet end of the air duct, and a bottom edge of each plate is fitted on the top end of the essential oil output duct; thereby compressed air from the air duct flows through the extended airflow passage defined by the pair of extending plates therebetween and blows to the outlet port of the essential oil output duct.

The aroma diffuser of the present invention has an essential oil bottle installed outside the host by setting a mounting ring on the outside of the host, which is convenient for observing the amount of essential oil, more convenient to assemble/disassemble and replace the essential oil bottle.

Further, an aromatherapy nebulizer of the present invention has a nebulizer cap with inseparable one-piece air duct and essential oil essential oil output duct, which is easy to manufacture and assemble, not easy to be damaged, no displacement during work, so that the aromatherapy nebulizer can atomize the essential oil uniformly and stably with high efficiency.

Other advantages and features of the present invention will be fully understood by reference to the following specification in conjunction with the accompanying drawings, in which like reference signs denote like components of structure.

DETAILED DESCRIPTION OF THE INVENTION

The embodiments of the present invention and the features in the embodiments can be combined with each other. The following describes the present invention in further detail with reference to the drawings and specific embodiments.

Refer to FIGS. 1-5, an aromatherapy nebulizer 100 provided in accordance with the embodiments of the present invention, comprises a nebulizer cap 1 and an essential oil bottle 2. The essential oil bottle 2 and the nebulizer cap 1 are threadedly connected, and the dip tube 3 extends from the nebulizer cap 1 into the bottom of the essential oil bottle 2. The essential oil bottle 2 contains liquid essential oil, and the essential oil is absorbed into the nebulizer cap 1 by the dip tube 3 to form a mist and then sprayed outside from a spray nozzle 110 of the aromatherapy nebulizer 100.

Figure 1:
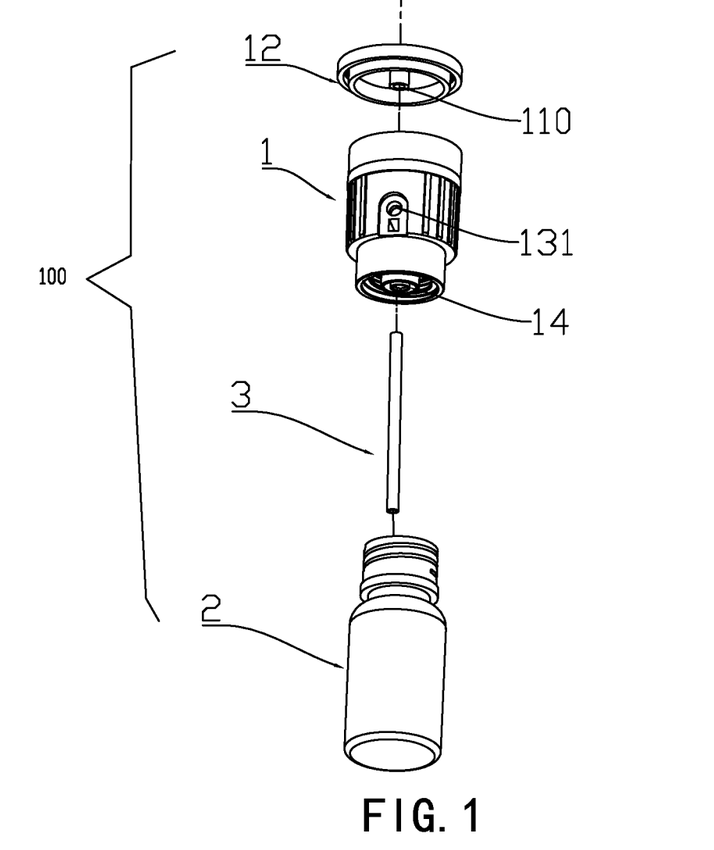
FIG. 1 is an exploded view of an aromatherapy nebulizer in accordance with an embodiment of the present invention.
Figure 2:
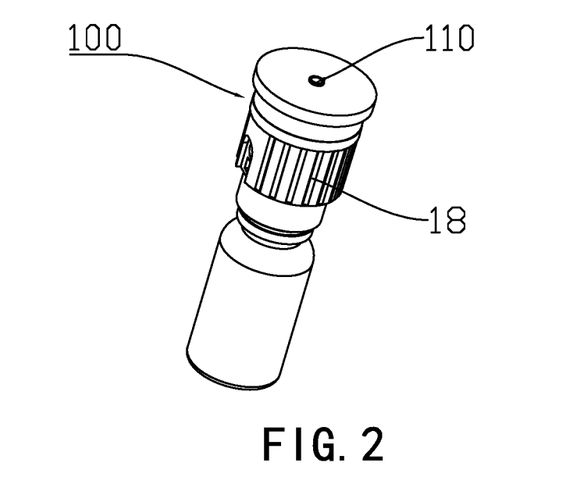
FIG. 2 is a perspective view of the aromatherapy nebulizer in accordance with the embodiment of the present invention.

The mouth of the essential oil bottle 2 is provided with threads. The lower sidewall of the nebulizer cap 1 is provided with internal threads, which are threadedly connected with the mouth of the essential oil bottle 2.

The nebulizer cap 1 comprises a bottom wall 19 and a side wall 10 around the bottom wall 19 which has an upper sidewall defining an air chamber 11 therein, and has a lower sidewall connected with the essential oil bottle. The aromatherapy nebulizer 100 sets a spray nozzle 110 communicating the air chamber 11 with the external environment; the air chamber is communicated with the dip tube 3 for transporting the liquid essential oil from essential oil bottle 2 into the air chamber 11 for forming essential oil mist which is ejected to the external environment through the spray nozzle 110.

In this embodiment, the upper sidewall around the bottom wall 19 of the nebulizer cap 1 forms an opening top and defines the air chamber 11 therein; the aromatherapy nebulizer 100 further comprises a top cover 12 to close the opening top of the nebulizer cap 1; and the spray nozzle 110 is formed in the top cover.

Figure 3:
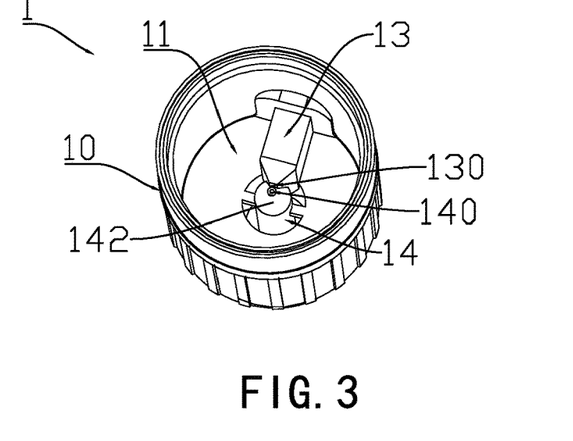
FIGS. 3-5 are perspective views of nebulizer caps in accordance with different embodiments of the present invention.

Preferably, the nebulizer cap 1 is an integral and inseparable one-piece structure, and may be made from plastic by an integral injection molding. An air duct 13 and an essential oil output duct 14 are integrally (or in-one-piece) formed in the nebulizer cap 1, that is, the air duct 13 and essential oil output duct 14 are inseparable parts of the nebulizer cap 1. The air duct 13 is used to deliver compressed air from the air pump to the air chamber 11; the essential oil output duct 14 is connected with the dip tube 3, and is used to deliver the liquid essential oil sucked by the dip tube 3 into the air chamber 11. The air duct 13 is formed on the bottom wall in the air chamber 11, and has an outlet port 130 thereof located in the air chamber 11, and an inlet end thereof extending through the sidewall of the chamber 11 to form a through hole in the sidewall of the nebulizer cap 1 as the air inlet port 131 of the nebulizer cap 1, an outlet of the air pump is connected with the air inlet port 131 of the air duct 13. In this embodiment, the air duct 13 is located horizontally on the bottom wall 19. The essential oil output duct 14 is formed vertically through the bottom wall 19.

Specifically, an outlet end 132 of the air duct 13 is located in the air chamber 11 and forms the outlet port 130; the essential oil output duct 14 passes through the bottom wall 19 of the nebulizer cap 1, a lower end thereof connects the dip tube, and a top end (or an outlet end) 142 thereof extends upwards into the air chamber 11 and forms the outlet port 140. Preferably, the outlet ports 130,140 of the air duct 13 and the essential oil output duct 14 are adjacent to each other; and the outlet port 130 of the air duct 13 is located at top side the outlet port 140 of the essential oil output duct 14, thereby the airflow from the outlet port 130 of the air duct 13 blows to the outlet port 140 of the essential oil output duct 14.

In one embodiment, the nebulizer cap 1 is circular, and has a circular bottom wall 19 with an annular sidewall 10 therearound. The air duct 13 is formed on the bottom wall with the outlet port 130 thereof extending at a center (including near the center) of the air chamber 11 (or the bottom wall 19), and radially extends to the sidewall 10. The air duct 13 extends through the sidewall of the air chamber 11, and the port forms an air inlet port 131 of the nebulizer cap. The essential oil output duct 14 extends through the bottom wall 19 of the air chamber 11 and is used for connecting the dip tube 3. The outlet port 140 of the essential oil output duct 14 is located at the center (including close to the center) of the circular bottom wall 19 of the air chamber 11, the essential oil output duct 14 extends along the central axis, and the outlet port 140 of the essential oil output duct 14 extends upward from the center of the bottom wall 19 to a certain height. The air duct 13 is arranged relatively horizontally, that is, horizontally along the circular bottom wall, and the essential oil output duct 14 is arranged along a vertical center axis of the circular bottom wall 19. The axis direction is set vertically. The outlet port 130 of the air duct 13 and the outlet port 140 of the essential oil output duct 14 are arranged in the air chamber 11 with the air-flow directions intersected (for example, perpendicular to each other). The outlet port 130 of the air duct 13 and the outlet port 140 of the essential oil output duct 14 are adjacent to each other. Specifically, the outlet port 130 of the air duct 13 is located at top side of the outlet port 140 of the essential oil output duct 14, and keep the airflow from the outlet port 130 blows towards the outlet port 140.

The air duct 13 and the essential oil output duct 14 are integrated with the nebulizer cap 1 in an injection molding of plastic materials. In accordance with an embodiment of the present invention, referring to FIG. 3, an outlet end 132 of the air duct 13 is tapered and narrowed towards the outlet port 130, so that the outlet port 130 forms nozzle-shaped to enhance the airflow and increase the airflow speed from the outlet port 130. The airflow horizontally blows to the outlet port 140 and forms negative pressure in the outlet port 140 of the essential oil output duct 14, then the essential oil in the dip tube 3 is sucked upward and forms mist in the air chamber 11. Further, a top end (or an outlet end) 142 of the essential oil output duct 14 also is tapered and narrowed towards the outlet port 140, so that the outlet port 140 forms nozzle-shaped, which can increase the ejection speed of the liquid essential oil. When the airflow blows from the outlet port 130 of the air duct 13 above the outlet port 140, the tapered end surface of the outlet port 140 can reduce the resistance of the airflow. The outlet ports 130 and 140 have no displacement during work due to the integrated air duct 13 and the essential oil output duct 14, the liquid essential oil can be evenly and stably formed into fine mist in the air chamber 11, thereby, the aromatherapy nebulizer 100 can evenly and stably spay fine mist essential oil to outside from the spray nozzle 110.

Figure 5:
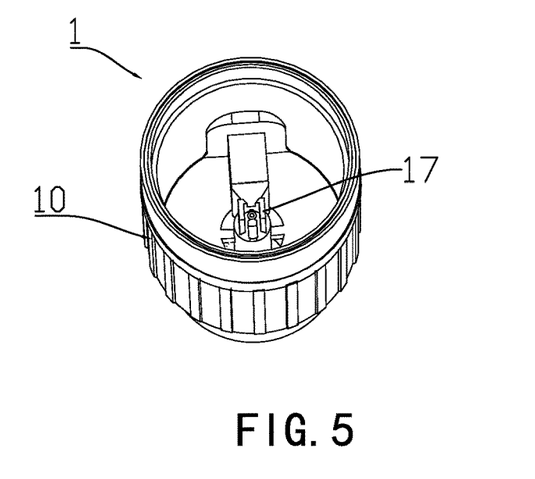

Referring to FIG. 5, a pair of extending plates 17 is set beside the outlet port 130 of the air duct 13 so as to forms an extended airflow passage of the air duct 13, both the outlet ports 130 and 140 are located between the pair of extending plates. In one embodiment, the pair of extending plates are parallel to each, has one end of each plate fitted on and connected with the tapered outlet end 132 of the air duct 13, and has the bottom edge of each plate fitted on the tapered top end 142 of the essential oil output duct 14. Air from the air duct 13 flows through the extended airflow passage defined by the pair of extending plates 17 therebetween and blows to the outlet port 140.

In some embodiments, a diameter of the outlet port 130 of the air duct 13 ranges from 0.05 mm to 1 mm; a diameter of the outlet port 140 of the essential oil output duct 14 ranges from 0.1 mm to 2 mm; a horizontal distance between the outlet port 130 of the air duct 13 and the outlet port 140 of the essential oil output duct 14 is 0.2 mm-5 mm.

Figure 4:
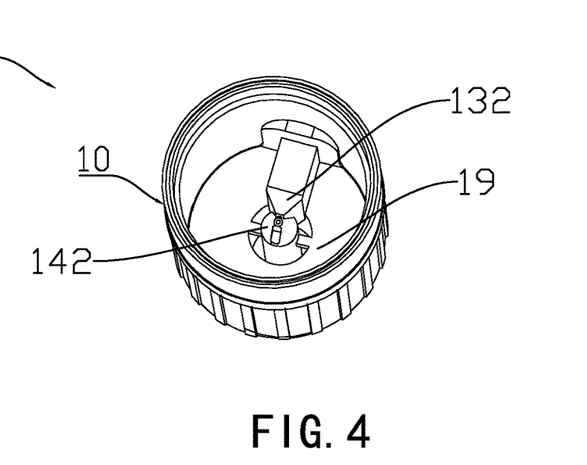

The nebulizer cap 1 is provided with a positioning structure such as a clamping structure, a fitting structuring, protrusion/groove structures and so on. In this embodiment, the nebulizer cap 1 forms grooves/protrusion ribs on the sidewall 10 of the nebulizer cap 1. Specifically, one or more protrusion ribs 18 are vertically and parallel arranged on the annular sidewall 10 of the nebulizer cap 1 along a height direction of the sidewall. The positioning structure of the nebulizer cap 1 is engaged in the mounting ring 50 of the aroma diffuser 1000 to facilitate the installation of aromatherapy nebulizer to the aroma diffuser 1000.

Referring to FIGS. 6-12, the present invention also provides an aroma diffuser 1000, which includes a host 500 and the aromatherapy nebulizer 100 installed outside the host 500. A mounting ring 50 is provided from a sidewall 52 of the host 500 and extends outwards, the aromatherapy nebulizer 100 is inserted into the mounting ring 50 and is fastened via the nebulizer cap 1 engaged with the mounting ring 50. The aromatherapy nebulizer 100 passes through the mounting ring 50 from top to bottom, and the nebulizer cap 1 and the mounting ring 50 can be snap-fitted. The mounting ring 50 is sleeved around the outside of the nebulizer cap 1, the aromatherapy nebulizer 100 (or the nebulizer cap 1) is supported by the mounting ring 10 in a pluggable manner. In this embodiment, the aromatherapy nebulizer 100 can be inserted up and down inside the mounting ring 50, the rotation therebetween may be limited due to an engagement therebetween or via positioning structures thereof.

Figure 6:
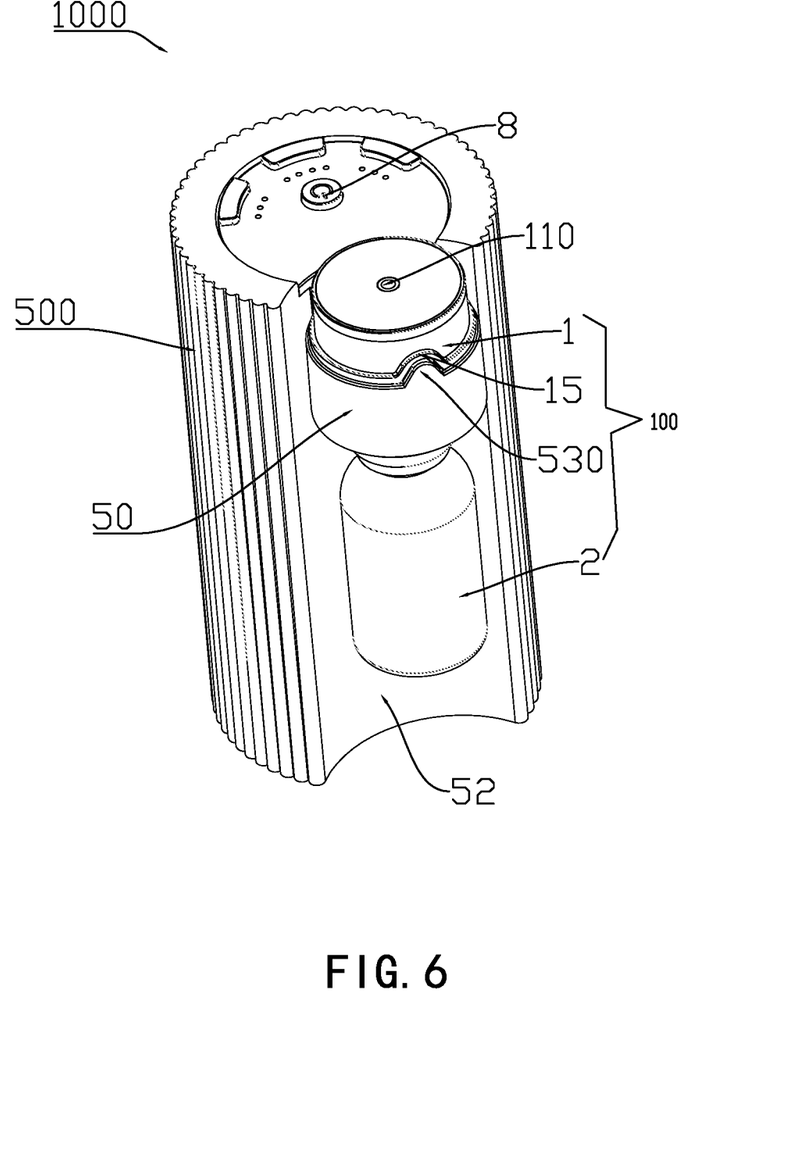
FIG. 6 is a perspective view of an aroma diffuser in accordance with a first embodiment of the present invention.
Figure 7:
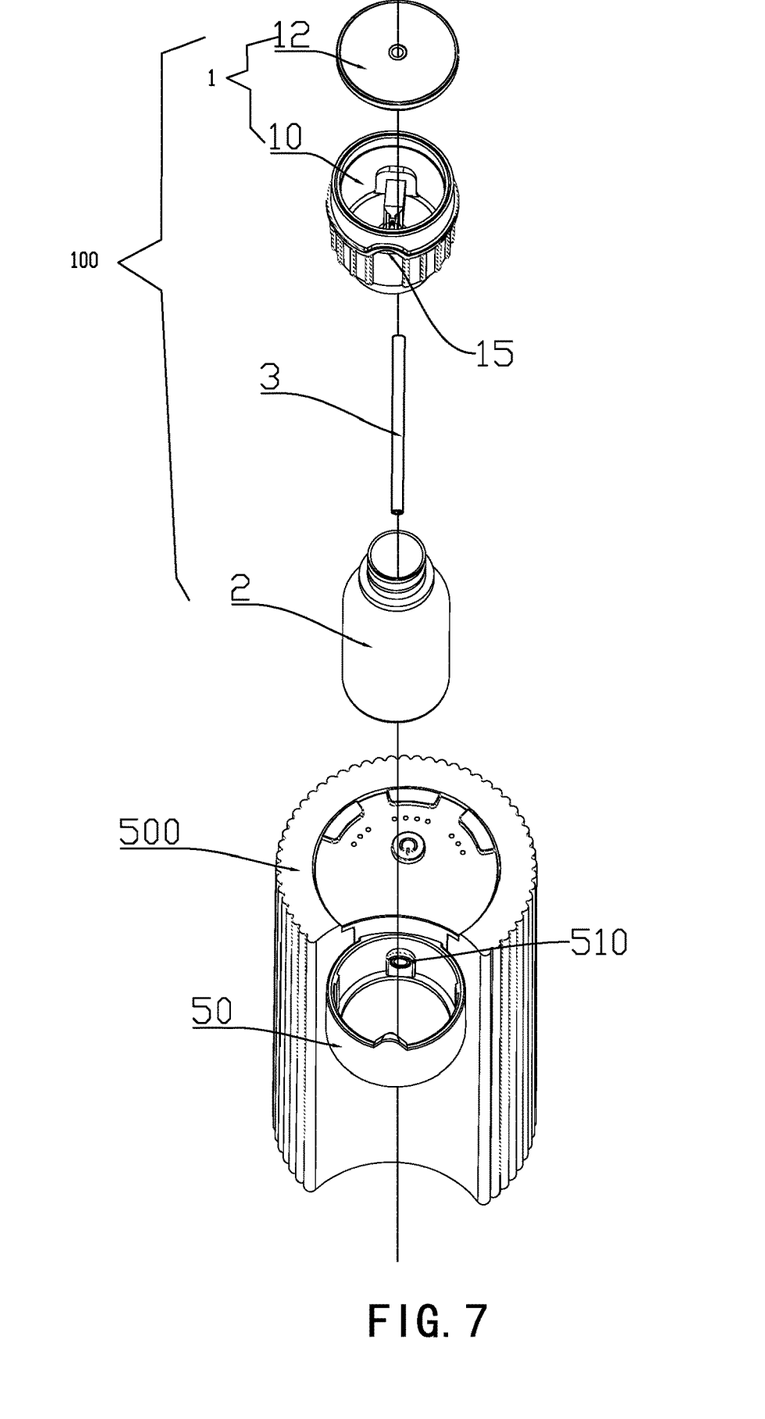
FIG. 7 is a partially exploded view of the aroma diffuser in accordance with the first embodiment of the present invention.

In an embodiment, the nebulizer cap 1 forms a protruding flange 16 thereon, the aromatherapy nebulizer 100 is inserted downwards into the mounting ring 50, and the protruding flange 16 is clamped on the top edge of the mounting ring 50. Preferably, the protruding flange 16 is a protruding ring around the sidewall of the nebulizer cap 1, the protruding ring has a larger diameter than that of the mounting ring 50.

The mounting ring 50 and the nebulizer cap 1 are engaged with each other so that the aromatherapy nebulizer 100 can be inserted and fastened in or pulled out from the mounting ring 50. The nebulizer cap 1 can be further positioned or installed in place and cannot rotate freely relative to the mounting ring 50. A positioning structure or fitting structure is formed between the mounting ring 50 and the nebulizer cap 1, which allows the nebulizer cap 1 is pluggable in the mounting ring 50 while limits the rotation therebetween.

Preferably, the sidewall 52 of the host 500 has a concave curved surface for holding the aromatherapy nebulizer 100. Specifically, the concave curved surface of the sidewall 52 has a shape adapted for the essential oil bottle 2 and the circular nebulizer cap 1

Figure 8:
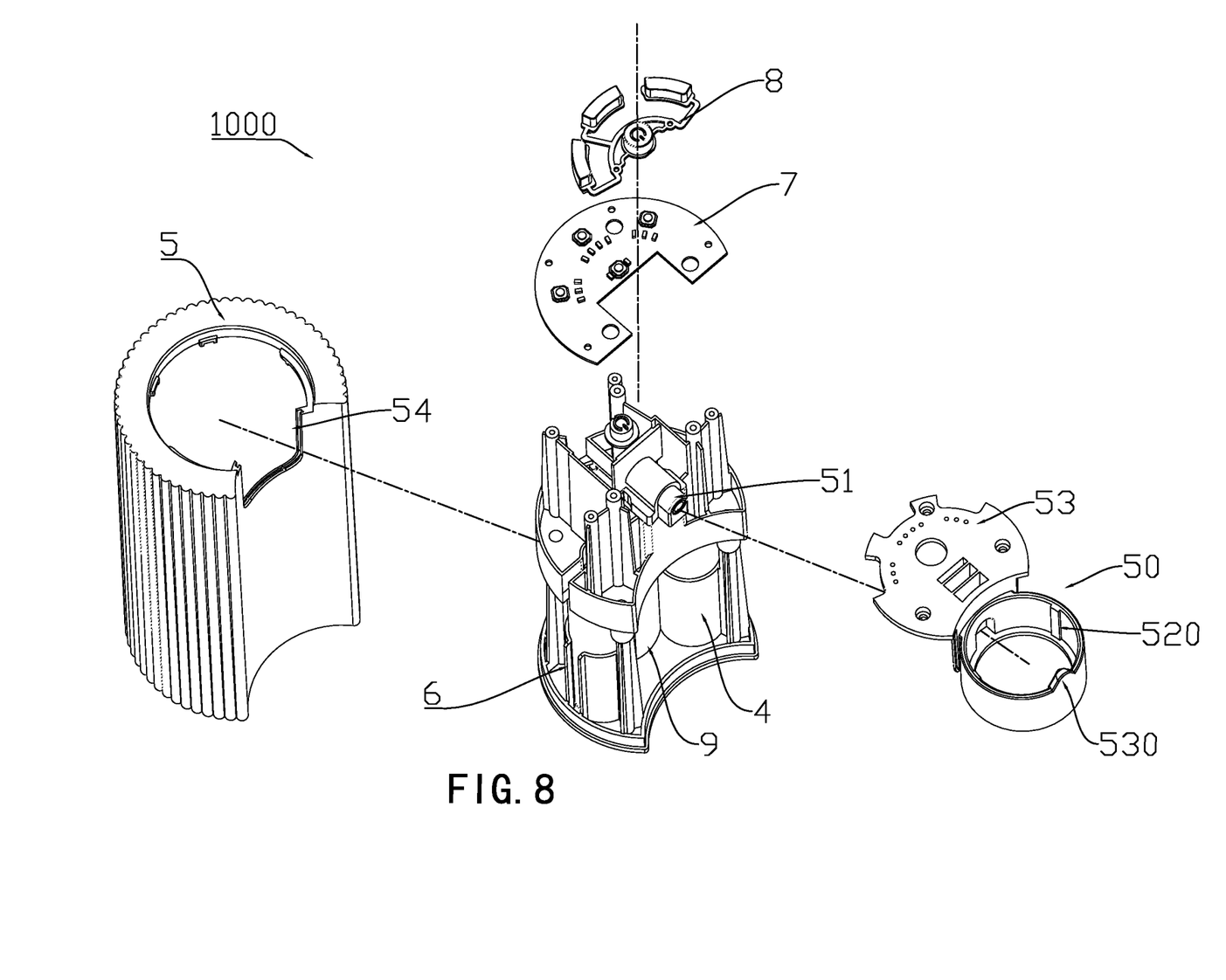
FIG. 8 is an exploded view of the aroma diffuser in accordance with the first embodiment of the present invention.
Figure 9:
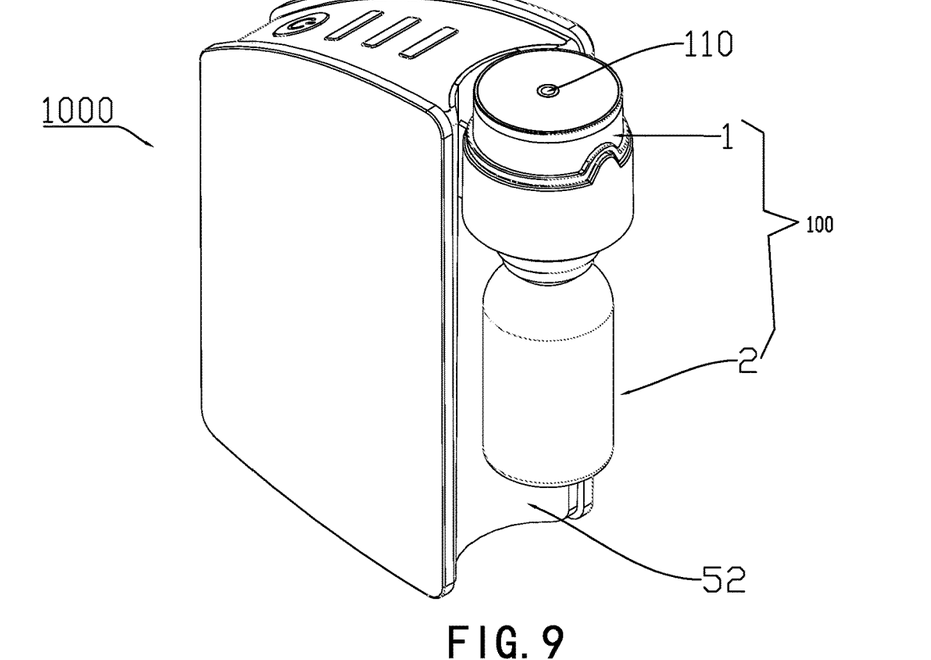
FIG. 9 is a perspective view of the aroma diffuser in accordance a second embodiment of the present invention.

The host 500 includes a housing 5 in which a framework 6 is provided. The host 500 also includes an air pump 4 installed by the framework 6, a control circuit board 7, a button panel 8, a battery 9, and an air connecting piece 51. The button panel 8 is electrically connected to the control circuit board 7. The air connecting piece 51 is fixed on the framework 6, and has a through air passage 510 inside for connecting the air outlet of the air pump 4 and the air inlet port 131 of the nebulizer cap 1 so as to transport compressed air from the air pump 4 to the air chamber 11 of the nebulizer cap 10. In one embodiment, the air connecting piece 51 is made of silicone.

The control circuit board 7 is electrically connected to the air pump 4, and the control circuit board 7 controls the air pump 4 to work. The battery 9 is electrically connected to the control circuit board 7 and the air pump 4 for power supply.

Start the air pump 4 by operating the button panel 8, the air outlet of the air pump 4 is connected to the air inlet port 131 of the air duct 13 through the air connecting piece 51, so that compressed air from the air pump 4 is delivered to the air chamber 11, air flows out from the outlet port 130 of the air duct 13, blows away the air in the outlet port 140 of the outlet duct 14 to form a negative pressure. As a result, the liquid essential oil in the essential oil bottle 2 rises along the dip tube 3 into the essential oil output duct 14 and is ejected from the outlet port 140 to form fine mist of essential oil. Under the air pressure in the air chamber 11, the essential oil mist is sprayed out from the spray nozzle 110 of the nebulizer cap 1.

The aromatherapy nebulizer 100 is installed and fixed by the mounting ring 50 which is provided outside of the housing 5, so that the aromatherapy nebulizer 100 is installed and exposed outside of the host 500, which facilitates real-time observation of the remaining amount of liquid essential oil in the essential oil bottle 2. The essential oil bottle 2 is a transparent bottle or has a visible transparent part to observe the liquid level. The aromatherapy nebulizer 100 is directly inserted into the mounting ring 50 for installation which is convenient for installation and replacement. In one embodiment, the mounting ring 50 may be integrally formed on the housing 5 in one piece and protrude outwards on the sidewall 52. In another embodiment, the mounting ring 50 may extend outwards from an opening 54 of the sidewall 52. Specifically, the mounting ring 50 can be provided with a fastening piece such as an installation disk 53 (referring to FIG. 8), the installation disk 53 is fixed by the framework 6, and the mounting ring 50 extends outward from the opening 54 in the sidewall 52 of the housing 5. The mounting ring 50 defines a through hole in its annular wall for the air connecting piece 51 to pass through or used as the outlet of the air passage 510 of the air connecting piece 51, and is aligned and connected with the air inlet port 131 of the aromatherapy nebulizer 100 in the mounting ring 50.

Figure 10:
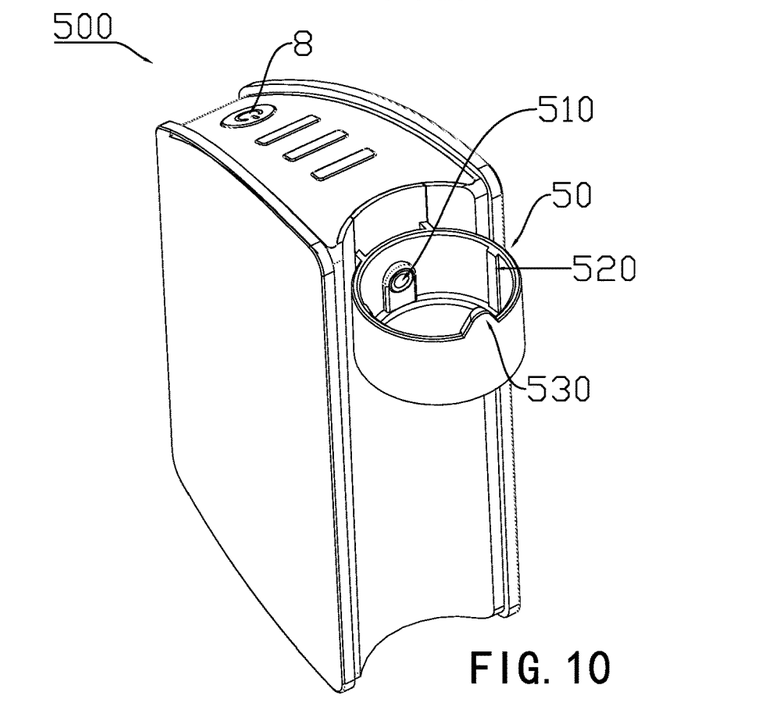
FIG. 10 is a perspective view of a host of the aroma diffuser in accordance with the second embodiment of the present invention.
Figure 11:
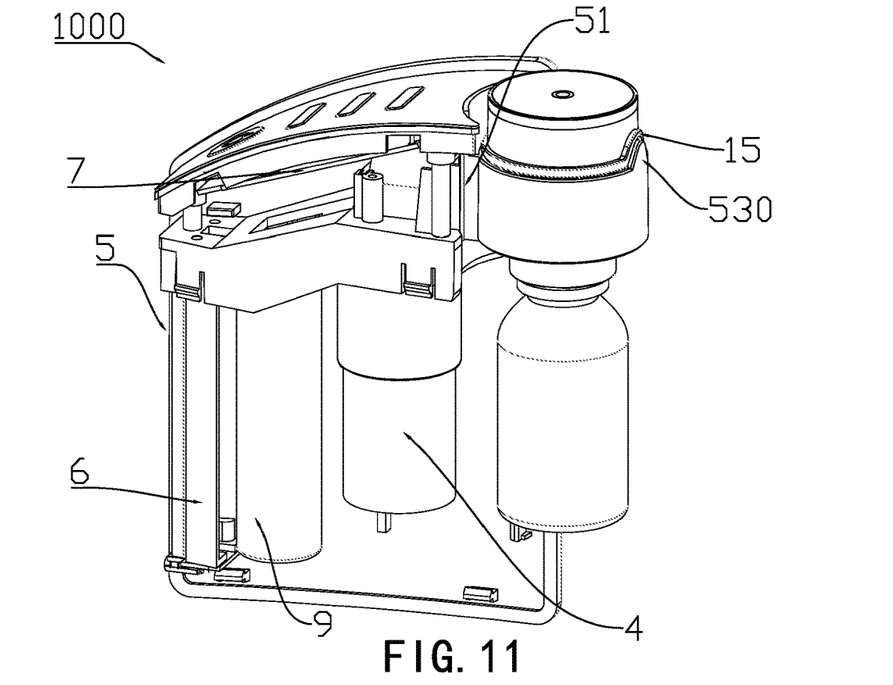
FIG. 11 is a schematic diagram of the aroma diffuser with one side panel removed in accordance with the second embodiment of the present invention.
Figure 12:
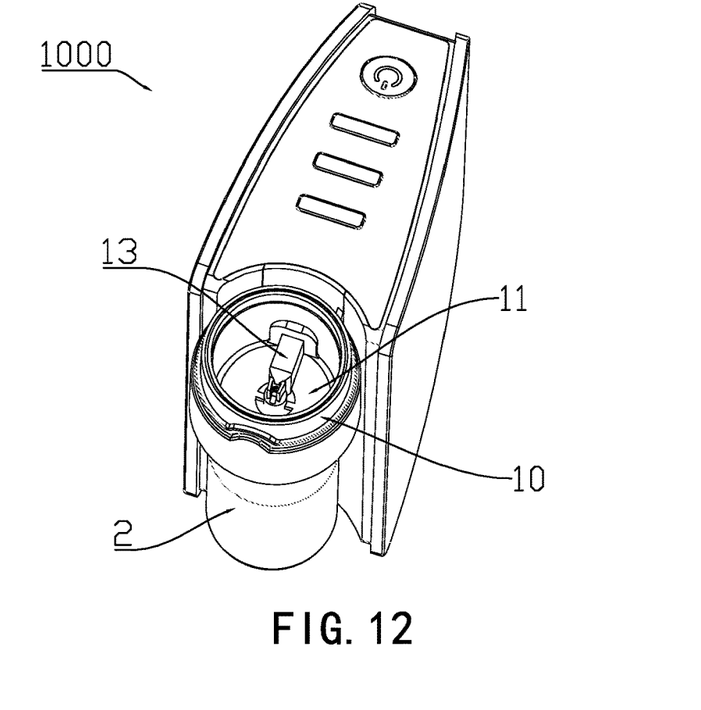
FIG. 12 is a perspective view of the aroma diffuser in accordance with the second embodiment of the present invention with a top cover of the aromatherapy nebulizer removed.

The mounting ring 50 and the nebulizer cap 1 are engaged each other. In one embodiment, the nebulizer cap 1 is provided with vertical protrusion ribs 18 on outside wall, and the mounting ring 50 is correspondingly provided with receiving grooves or ribs 520 on an inner wall thereof, so that the nebulizer cap 1 is fitted in the mounting ring 50 with the grooves on the inner wall of the mounting ring 50 receiving and stopping the ribs 18 on outside wall of the nebulizer cap 1; or the ribs 520 on the inner wall of the mounting ring 50 abut against the ribs 18 on the sidewall 10 of the nebulizer cap 1. Therefore, when the aromatherapy nebulizer 100 is installed in place, it cannot rotate freely in the mounting ring 50.

The inner wall of the mounting ring 50 is provided with three (not limited to three) ribs 520 along the height direction, and the annular sidewall of the nebulizer cap 1 may be provided with one or more ribs.

The nebulizer cap 1/mounting ring 50 is provided with a limit or positioning structure further. Specifically, the outer wall of 50 is provided with a positioning protrusion 530 which are received in the positioning grooves 15 in the sidewall of the nebulizer cap 1 for alignment and positioning. When the aromatherapy nebulizer 100 is inserted into the mounting ring 50, the positioning structures are aligned or fitted each other, so that the air inlet port 131 in the nebulizer cap 1 is aligned and connected with the through hole in the mounting ring 50.

The shape of the host 500 can be set as required. The aroma diffuser 1000 shown in FIGS. 6-8 is a desktop aromatherapy device, and the host is in the shape of a cylinder or other stable structure. The aroma diffuser 1000 shown in FIGS. 9-12 is a vehicle-mounted aromatherapy device.

In the present invention, the mounting ring 50 is provided to realize the aromatherapy nebulizer 100 externally placed outside the host 500. The structure is simple, it is convenient for installation/disassembly or replacement of the aromatherapy nebulizer 100, and it is convenient to observe the remaining amount of essential oil in the essential oil bottle 2.

In the description of the present invention, it should be understood that the terms, "upper", "lower", "vertical", "horizontal", "top", "bottom", "inner", "outer", etc. are based on the orientation or positional relationship shown in the drawings, and are only for the convenience of describing the present invention and simplifying the description, cannot be understood as a limitation of the present invention.

Although the embodiments of the present invention have been shown and described, for those of ordinary skill in the art, it will be understood that various changes can be made to these embodiments without departing from the principle and spirit of the present invention. Modifications, substitutions and variations shall all belong to the scope of the present invention; the protection scope of the present invention is defined by the appended claims and their equivalents.

What the invention claimed is:

1. An aroma diffuser, comprising a host and an aromatherapy nebulizer; the host having an air pump received therein; the air pump having an air inlet port and an air outlet port; the aromatherapy nebulizer comprising a nebulizer cap and an essential oil bottle with a dip tube extending from the nebulizer cap into the essential oil bottle for sucking liquid essential oil up; wherein the host sets a mounting ring extending outwards from a sidewall thereof, the aromatherapy nebulizer is installed in the mounting ring in such way that the aromatherapy nebulizer is able to be plugged in or pulled out up and down through the mounting ring, whereby the aromatherapy nebulizer is installed externally to the host; the nebulizer cap comprises a bottom wall and a side wall around the bottom wall which has an upper sidewall defining an air chamber therein, and has a lower sidewall connected with the essential oil bottle; the aromatherapy nebulizer sets a spray nozzle communicating the air chamber with the external environment; the air chamber is communicated with the air outlet port of the air pump for transporting compressed air from the air pump into the air chamber, and is communicated with the dip tube for transporting the liquid essential oil from essential oil bottle into the air chamber for forming essential oil mist which is ejected to the external environment through the spray nozzle.

2. The aroma diffuser of claim 1, wherein the mounting ring substantially is an annular wall which is open and through up and down, and is adapted for the nebulizer cap; the upper sidewall around the bottom wall of the nebulizer cap forms an opening top and defines the air chamber therein; the aromatherapy nebulizer further comprises a top cover to close the opening top of the nebulizer cap; and the spray nozzle is formed in the top cover.

3. The aroma diffuser of claim 1, wherein the sidewall of the host for setting the mounting ring has a concave curved surface for holding the aromatherapy nebulizer; the concave curved surface of the sidewall has a shape adapted for the essential oil bottle and the nebulizer cap.

4. The aroma diffuser of claim 1, wherein the mounting ring is integrally formed in one piece with the sidewall of the host, and protrudes outwards on the sidewall; or, the mounting ring is fixed inside the host via a fastening piece formed on the mounting ring, and the mounting ring extends outwards from an opening defined in the sidewall of the host; or, the mounting ring is fixed on the sidewall of the host via fastening structures.

5. The aroma diffuser of claim 1, wherein an annular wall of the mounting ring defines a through hole for connecting airflow from the air outlet port of the air pump to the air chamber in the nebulizer cap when the aromatherapy nebulizer is installed in the mounting ring; the nebulizer cap defines an air inlet port communicated with the air chamber, the air inlet port of the nebulizer cap is aligned and connected with the through hole of the mounting ring when the aromatherapy nebulizer is installed in the mounting ring.

6. The aroma diffuser of claim 5, wherein an air connecting piece with an air passage inside is set in the host and extends in the through hole of the mounting ring; one end of the air connecting piece is connected with the air outlet port of the air pump, and the other end of the air connecting piece pass through the through hole of the mounting ring and extends to an inner wall of the mounting ring, whereby the air passage inside the air connecting piece connects the air outlet of the air pump with the air inlet port of the nebulizer cap when the aromatherapy nebulizer is installed in the mounting ring.

7. The aroma diffuser of claim 5, wherein when the aromatherapy nebulizer is installed in the mounting ring, the mounting ring is sleeved around the outside of the nebulizer cap, and the nebulizer cap is engaged with the mounting ring for fastening the aromatherapy nebulizer in the mounting ring.

8. The aroma diffuser of claim 7, wherein the nebulizer cap forms a protruding flange thereon, when the aromatherapy nebulizer is inserted into the mounting ring, the protruding flange is clamped on a top edge of the mounting ring; the protruding flange is a protruding ring around the sidewall of the nebulizer cap; the protruding ring has a larger diameter than that of the mounting ring; the nebulizer cap has a circular shape with an annular sidewall and a circular bottom wall.

9. The aroma diffuser of claim 7, wherein the nebulizer cap and the mounting ring form positioning structures therebetween; the positioning structures comprising one or more of a clamping structure, a fitting structuring, or protrusion/groove structures.

10. The aroma diffuser of claim 7, wherein the sidewall of the nebulizer cap forms one or more ribs along a height of the sidewall; the mounting ring is correspondingly provided with one or more receiving grooves or ribs on an inner wall thereof, whereby the nebulizer cap is fitted in the mounting ring with the one or more receiving grooves or ribs on the inner wall of the mounting ring engaged with the one or more ribs on the sidewall of the nebulizer cap, so that a rotation of the nebulizer cap relative to the mounting ring is limited, and the air inlet port of the nebulizer cap keeps aligned and connected with the through hole of the mounting ring when the aromatherapy nebulizer is installed in place.

11. The aroma diffuser of claim 10, wherein the nebulizer cap forms several ribs vertically and parallel spaced on the sidewall of the nebulizer cap; the mounting ring forms several ribs vertically and parallel spaced on the inner wall of the mounting ring along a height of the mounting ring so as to abut against the ribs on the sidewall of the nebulizer cap when the nebulizer cap is fitted in the mounting ring.

12. The aroma diffuser of claim 8, wherein the nebulizer cap and the mounting ring form grooves/protrusion engaging structure for positioning and limiting the nebulizer cap in the mounting ring.

13. The aroma diffuser of claim 12, wherein the nebulizer cap forms a groove on the sidewall thereof, and the mounting ring forms a protrusion upwards from a top edge thereof, and the protrusion is able to be received the groove; the groove is defined in the protruding flange.

14. The aroma diffuser of claim 1, wherein the nebulizer cap integrally forms an air duct and an essential oil output duct in one piece together; the air duct connects the air outlet port of the air pump with the air chamber in the nebulizer cap so as to deliver compressed air from the air pump to the air chamber; the essential oil output duct connects the dip tube with the air chamber so as to deliver the liquid essential oil sucked in the dip tube into the air chamber.

15. The aroma diffuser of claim 14, wherein the air duct is formed on the bottom wall of the nebulizer cap, an inlet end of the air duct passes through the sidewall of the nebulizer cap and forms an air inlet port of the nebulizer cap communicated with the air chamber via the air duct, and an outlet end of the air duct is located in the air chamber and forms an outlet port; the essential oil output duct passes through the bottom wall of the nebulizer cap, a lower end thereof connects the dip tube, and a top end thereof extends upwards into the air chamber and forms an outlet port.

16. The aroma diffuser of claim 15, wherein the outlet ports of the air duct and the essential oil output duct are adjacent to each other; and the outlet port of the air duct is located at top side the outlet port of the essential oil output duct, whereby the airflow from the outlet port of the air duct blows to the outlet port of the essential oil output duct.

17. The aroma diffuser of claim 15, wherein the outlet end of the air duct is tapered and narrowed towards the outlet port of the air duct; the top end of the essential oil output duct is tapered and narrowed towards the outlet port of the essential oil output duct; a diameter of the outlet port of the air duct ranges from 0.05 mm to 1 mm; a diameter of the outlet port of the essential oil output duct ranges from 0.1 mm to 2 mm; a horizontal distance between the outlet port of the air duct and the outlet port of the essential oil output duct is 0.2 mm-5 mm.

18. The aroma diffuser of claim 15, wherein the nebulizer cap is circular such that the bottom wall is circular and the side wall is annular, the outlet ports of the air duct and the essential oil output duct extend at a center of the circular bottom wall; the essential oil output duct is arranged along a vertical center axis of the circular bottom wall; the air duct and the essential oil output duct are integrated with the nebulizer cap in an injection molding of plastic materials.

19. The aroma diffuser of claim 15, wherein a pair of extending plates is set beside the outlet port of the air duct so as to form an extended airflow passage of the air duct, both the outlet ports of the air duct and the essential oil output duct are located between the pair of extending plates; the pair of extending plates are parallel to each, one end of each plate is fitted on and connected with the outlet end of the air duct, and a bottom edge of each plate is fitted on the top end of the essential oil output duct; whereby compressed air from the air duct flows through the extended airflow passage defined by the pair of extending plates therebetween and blows to the outlet port of the essential oil output duct.

20. The aroma diffuser of claim 1, further comprising a control circuit board, a battery and a button panel which is electrically connected to the control circuit board; the control circuit board is electrically connected to the air pump, and the battery is electrically connected to the control circuit board and the air pump for power supply.

* * * * *